United States Patent
Dhall

(10) Patent No.: US 10,485,698 B2
(45) Date of Patent: Nov. 26, 2019

(54) SOLID CONDUCTION INDUCED HYPOTHERMIA DEVICES

(71) Applicant: Sanjay Dhall, Mill Valley, CA (US)

(72) Inventor: Sanjay Dhall, Mill Valley, CA (US)

(73) Assignee: GREAT CIRCLE TECHNOLOGIES, INC., Mill Valley, CA (US)

( * ) Notice: Subject to any disclaimer, the term of this patent is extended or adjusted under 35 U.S.C. 154(b) by 431 days.

(21) Appl. No.: 15/369,391

(22) Filed: Dec. 5, 2016

(65) Prior Publication Data

US 2017/0079837 A1    Mar. 23, 2017

Related U.S. Application Data

(63) Continuation-in-part of application No. 14/257,135, filed on Apr. 21, 2014.

(60) Provisional application No. 61/814,964, filed on Apr. 23, 2013, provisional application No. 62/262,501, filed on Dec. 3, 2015.

(51) Int. Cl.
*A61F 7/12*    (2006.01)
*A61F 7/02*    (2006.01)
*A61F 7/00*    (2006.01)

(52) U.S. Cl.
CPC .................. *A61F 7/12* (2013.01); *A61F 7/02* (2013.01); *A61F 2007/0008* (2013.01); *A61F 2007/0018* (2013.01); *A61F 2007/0075* (2013.01); *A61F 2007/0233* (2013.01); *A61F 2007/0234* (2013.01); *A61F 2007/126* (2013.01)

(58) Field of Classification Search
None
See application file for complete search history.

(56) References Cited

U.S. PATENT DOCUMENTS 5,837,003 A * 11/1998 Ginsburg .................. A61F 7/12
                                                                    607/106
6,146,411 A   11/2000 Noda
6,517,534 B1   2/2003 Mcgovern et al.
(Continued)

FOREIGN PATENT DOCUMENTS

| JP | 2006-141993 | 6/2006 |
|---|---|---|
| JP | 2011-083315 | 4/2011 |
| WO | WO-2004/032720 | 4/2004 |

OTHER PUBLICATIONS

Dhall, U.S. Office Action dated Sep. 24, 2018, directed to U.S. Appl. No. 14/257,135; 15 pages.
(Continued)

*Primary Examiner* — Kaitlyn E Smith
(74) *Attorney, Agent, or Firm* — Morrison & Foerster LLP

(57) ABSTRACT

Medical devices for inducing hypothermia are disclosed. Induced hypothermia is a treatment used to reduce secondary complications caused by reduced oxygen and blood flow during traumatic injuries and surgeries. However, induced hypothermia also has negative side effects such as shivering and lowered immune system. These devices incorporate Highly-Oriented Pyrolytic Graphite (HOPG) for solid conduction to lower the temperature at targeted locations on and inside the body. The benefits of incorporating HOPG include: highly efficient heat conduction, flexibility in design and manufacture, reduction of dependence on inefficient and unstable fluid-filled implants and catheters, and anti-thrombotic effects.

3 Claims, 7 Drawing Sheets

(56) References Cited

U.S. PATENT DOCUMENTS

| | | | |
|---|---|---|---|
| 6,948,322 B1* | 9/2005 | Giblin | A41D 13/005 62/259.3 |
| 7,822,485 B2 | 10/2010 | Collins | |
| 8,123,789 B2* | 2/2012 | Khanna | A61F 7/12 607/105 |
| 8,353,942 B2 | 1/2013 | Merrill | |
| 9,180,042 B2 | 11/2015 | Collins | |
| 9,358,138 B2* | 6/2016 | Kelley | A61F 7/02 |
| 9,522,081 B2* | 12/2016 | D'Ambrosio | A61F 7/12 |
| 9,629,203 B1* | 4/2017 | Downs, Jr. | A41D 31/065 |
| 9,894,944 B2* | 2/2018 | Brooks | A41D 13/0053 |
| 9,981,137 B2* | 5/2018 | Eiger | A61N 1/37 |
| 10,085,879 B2* | 10/2018 | Pezzi | A61F 7/007 |
| 10,172,739 B2* | 1/2019 | Benyaminpour | A61F 7/02 |
| 2002/0040717 A1 | 4/2002 | Dobak, III | |
| 2002/0198579 A1* | 12/2002 | Khanna | A61F 7/12 607/105 |
| 2004/0034399 A1* | 2/2004 | Ginsburg | A61F 7/123 607/96 |
| 2007/0005121 A1 | 1/2007 | Khanna | |
| 2007/0270926 A1* | 11/2007 | Serrano Molina | A41D 13/0053 607/108 |
| 2008/0077088 A1 | 3/2008 | Collins | |
| 2008/0077206 A1 | 3/2008 | Collins | |
| 2010/0107657 A1* | 5/2010 | Vistakula | A41D 13/005 62/3.5 |
| 2010/0280438 A1 | 11/2010 | Thomas | |
| 2011/0029050 A1 | 2/2011 | Eiefteriades | |
| 2012/0290052 A1* | 11/2012 | D'Ambrosio | A61F 7/12 607/113 |
| 2013/0025315 A1* | 1/2013 | Freeman | F28D 15/0241 62/259.3 |
| 2013/0197608 A1* | 8/2013 | Eiger | A61N 1/37 607/61 |
| 2014/0276715 A1 | 9/2014 | Shuman et al. | |
| 2014/0303697 A1* | 10/2014 | Anderson | A61B 18/02 607/104 |
| 2014/0303698 A1* | 10/2014 | Benyaminpour | A61F 7/02 607/107 |
| 2014/0316373 A1* | 10/2014 | Dhall | A61F 7/12 604/506 |
| 2015/0040300 A1* | 2/2015 | Murray | A62B 17/003 2/455 |
| 2015/0173432 A1* | 6/2015 | McCoy | A41D 13/0056 62/259.3 |
| 2016/0022483 A1 | 1/2016 | Collins | |
| 2016/0317846 A1* | 11/2016 | Murray | A62B 17/003 |
| 2016/0374411 A1* | 12/2016 | Brooks | A41D 13/0053 165/104.21 |
| 2017/0056240 A1* | 3/2017 | D'Ambrosio | A61F 7/12 |
| 2017/0145596 A1* | 5/2017 | Hays | A41D 31/28 |
| 2017/0164675 A1* | 6/2017 | Buchert | A42B 1/008 |
| 2018/0103694 A1* | 4/2018 | Fortenbacher | A41D 13/0051 |
| 2018/0264275 A1* | 9/2018 | Eiger | A61N 1/37 |
| 2018/0360652 A1* | 12/2018 | Ritrivi | A61F 7/12 |
| 2019/0091063 A1* | 3/2019 | Benyaminpour | A61F 7/02 |

OTHER PUBLICATIONS

Office Action dated Aug. 24, 2018, directed to CN Application No. 201480034015.8; 5 pages. (with English translation).

The Hypothermia After Cardiac Arrest Study Group, "Mid Therapeutic Hypothermia to Improve the Neurological Outcome after Cardiac Arrest," New England Journal of Medicine, 2002; 346(8):549-56.

Kammersgaard LP, et al., "Admission Body Temperature Predicts Long-Term Mortality After Acute Stroke: The Copenhagen Stroke Study," Stroke, 2002, 33(7):1759-82.

Krieger, DW, et al. "Cooling for acute ischemic brain damage (Cool Aid) An open pilot study of induced hypothermia in acute ischemic stroke," Stroke, 2001, 32(8); 1847-54.

Schwab S. et al., "Moderate hypothermia in the treatment of patients with severe middle cerebral artery infarction," Stroke, 1998, 29(12):2461-66.

Polderman KH, "Application of therapeutic hypothermia in the intensive care unit," Intensive Care Medicine, 2004, 30(5):757-69.

Saunders N, et al., "Barrier Mechanisms in the Brain, I. Adult Brain," Critical and Experimental Pharmacology and Physiology, 1999, 26 (1):11-19.

Shannon CN, et al., "The economic impact of ventriculoperitoneal shunt failure," Journal of Neurosurgery Pediatrics, 2011, 8:(6) 593.

Mori MD, et al., "An Epidural Cooling Catheter Protects the Spinal Cord Against ischemic injury in Pigs," The Annals of Thoracic Surgery, 2005, 80(5):1829-33.

Moomiae RM, et al., "Novel intracranial Brain Cooling Catheter to Mitigate Brain Injuries," J NeuroIntervent Surg. 2012, 4:130-133.

Polderman and Callaghan, "Equipment review: Cooling catheters to induce therapeutic hypothermia," Critical Care, 2006, 10:234.

Chesnut RM, et al., "A trial of intracranial-pressure monitoring in traumatic brain injury," New England Journal of Medicine, 2012, 367(26):2471-81.

Sosin, et al., "incidence of mild and moderate brain injury in the United States, 1991" Brain Injury, 1996, 10(1):46-54.

Taccone F. "When, where and how to initiate hypothermia after adult cardiac arrest," Minerva Anestesiol, 2011, 77, 927-33.

Diringer MN, "Treatment of fever in the neurologic intensive care unit with a catheter-based heat exchange system," Critical Care Medicine, 2004, 32(2):559-64.

Haugk M, et al., "Feasibility and efficacy of a new non-invasive surface cooling device in post-resuscitation intensive care medicine," Resuscitation, 2007, 75(1):76-81.

Flemming K et al., "Comparison of external and intravascular cooling to induce hypothermia in patients after CPR," GMS German Medical Science, 2006, 4:Doc4.

Wong GK, et al., "External Ventricular Drain Infection," Journal of Neurosurgery, 2007, 107(1):248.

Medexsupply, "Cincinnati Sub-Zero Blanketrol III Hyper-Hypothermia System," 2013, Available at (https://www.medexsupply.com/orthopedic-therapy-hot-cold-therapy-heating-units-gel-warmers-cincinnati-sub-zero-blanketrol-iii-hyper-hypothermia-system-x_pid-32065.html?products_id=32065).

Rutland-Brown W, et al., "incidence of traumatic brain injury in the United States," The Journal of Head Trauma Rehabilitation, 2006, 21(6):544.

Edsbagge M, "Spinal CSF absorption in healthy individuals," American Journal of Physiology:Regulatory, Integrative & Comparative Physiology, 2004, 58(6):R1450-R5.

Yoshida K, et al., Phase-contrast MR Studies of CSF Flow Rate in the Cerebral Aqueduct and Cervical Subarachnoid Space with Correlation-based Segmentation, Magnetic Resonance in Medical Sciences, 2009, 8(3):91-100.

Bondy GP, "Pathology 425 Cerebrospinal Fluid (CSF)," Department of Pathology and Laboratory Medicine at the University of British Columbia, 2011.

Dhall, Non-Final Office Action dated Jun. 17, 2016, directed to U.S. Appl. No. 14/257,135; 7 pages.

Dhall, Non-Final Office Action dated Dec. 7, 2016, directed to U.S. Appl. No. 14/257,135; 10 pages.

Examination Report No. 1 dated Jan. 22, 2018, directed to AU Application No. 2014257323; 5 pages.

Dhall, U.S. Office Action dated Jul. 5, 2017, directed to U.S. Appl. No. 14/257,135; 10 pages.

Dhall, U.S. Office Action dated Dec. 12, 2017, directed to U.S. Appl. No. 14/257,135; 11 pages.

International Search Report and Written Opinion dated Sep. 19, 2014 directed International Application No. PCT/US2014/034798; 8 pages.

Office Action dated Oct. 20, 2017, directed to CN Application No. 201480034015.8; 8 pages.

Extended Search Report dated Nov. 11, 2016, directed to EP Application No.14789033.9; 8 pages.

CDC Centers for Disease Control and Prevention, "Spinal Cord Injury (SCI): Fact Sheet," Available at http://www.cdc.gov/traumaticbraininsury/scifacts.html visited on Apr. 23, 2014. 4 pages.

(56) References Cited

OTHER PUBLICATIONS

Harris, et al., (2009) "Discrete Cerebral Hypothermia in the Management of Traumatic Brain Injury: A Randomized Controlled Trial," Journal of Neurosurgery, 110(6): 1256-1264.

Office Action dated Apr. 3, 2018, directed to JP Application No. JP-2016-510719; 6 pages. (Machine translation).

Penguin Cold Caps, "Cap information," Available at http://penguincoldcaps.co.nz/public/default.php?page=17 visited on Apr. 28, 2014. 2 pages.

Vidal CN, et al., (2008) "Three-dimensional mapping of the lateral ventricles in autism," Psychiatry Research: Neuroimaging, 163:106-115.

Dhall, U.S. Office Action dated Apr. 30, 2019, directed to U.S. Appl. No. 14/257,135; 18 pages.

Notice of Reasons for Refusal dated Feb. 26, 2019, directed to JP Application No. JP-2016-510719; 6 pages.

\* cited by examiner

SOLID CONDUCTION INDUCED HYPOTHERMIA DEVICES

CROSS-REFERENCE TO RELATED APPLICATION

This application claims the benefit of priority of U.S. Provisional Application 62/262,501, filed on Dec. 3, 2015, and is a continuation-in-part of U.S. patent application Ser. No. 14/257,135, which claims the benefit of priority of U.S. Provisional Application 61/814,964, filed on Apr. 23, 2013.

BACKGROUND OF THE INVENTION

1. Field of the Invention

The present invention relates to devices for inducing hypothermia.

2. Description of the Related Art

Induced therapeutic hypothermia and other medically-induced cooling methods are promising treatments with wide-ranging applications. The reduction of patients' body temperature during strokes, heart attacks and brain or spine injuries has been shown to reduce secondary complications caused by ischemia and other impairments to oxygen and blood flow. Induction of mild hypothermia has been hypothesized to significantly decrease intracranial pressure and secondary neurological injury. The Hypothermia after Cardiac Arrest Study Group. "Mild Therapeutic Hypothermia to Improve the Neurologic Outcome after Cardiac Arrest." New England Journal of Medicine 346.8 (2002): 549-56.

Hypothermia can be applied in many circumstances, including in emergency settings to mitigate damage, and during surgeries to reduce the risk of ischemia. Currently known methods of induced hypothermia include external cooling baths and blankets, and internal circulation of fluids and gasses, whether directly into the body or within delivery means such as balloon catheters. Many methods are aimed at inducing systemic hypothermia, i.e. hypothermia induced to the whole body. In fact, induction of systemic hypothermia is now the standard of care in the management of patients who survive cardiac arrest.

More specific applications of applied cooling methods include, but are not limited to, pain relief, prevention of chemotherapy induced hair loss, and reduction of discomfort of braces and casts. In addition, some devices seek to induce systemic hypothermia using localized techniques, because systemic hypothermia is associated with a host of negative side effects such as bleeding diathesis, shivering, arrhythmias, suppression of the immune system, and electrolyte imbalance. Some such devices focus on cooling the brain, for instance using cooling helmets. Others purport to deliver cooling directly to circulating fluids, for instance, the bloodstream (see U.S. Pub. No. 2002/0030717 A1), or cerebrospinal fluid (see U.S. Pat. No. 2007/0005121 A1). Inserts such as catheters are cooled using the circulation of fluid to the inserted device. These devices, however, are limited by the freezing point of the fluid, and they can rupture or leak fluid, resulting in dangerous contamination. Furthermore, balloon catheter use has been associated with increased risk of deep vein thrombosis (DVT) and clotting.

BRIEF SUMMARY OF THE INVENTION

Disclosed herein are devices for inducing therapeutic hypothermia using solid-to-solid conduction. These devices include garments that apply cooling to the body, both local and general, and insertable devices such as catheters, which use the flow of blood or cerebrospinal fluid to distribute cooling throughout the body. The devices use solid thermal conductive elements, safe to use in and on the human body, to transmit cooling temperatures from an external cooling element to sections of the device in contact with the body. In particular, the preferred solid thermal conductive and body-safe elements are comprised of Highly Oriented Pyrolytic Graphite sheets (HOPG), which have known anti-clotting effects.

HOPG, also known as graphite sheets, graphene, and PGS (Pyrolytic Graphite Sheets), is currently used in electronic applications for heat conductive properties. Hereinafter, the term "HOPG" will be used to refer to those currently known forms of synthetic graphite comprised of highly aligned graphite crystallites resulting in high thermal conductivity. The thermal conductivity of the HOPG is much higher than aluminum, steel, and even copper. For instance, 25 μm sheets demonstrate conductivity of up to 1700 W/m K, versus 300 W/m K for pure copper. Furthermore, HOPG can be produced in thin, flexible sheets and other shapes suitable to all kinds of medical devices.

BRIEF DESCRIPTION OF THE DRAWINGS

In the following drawings, like reference numbers have been used wherever possible to indicate like parts in different views.

DETAILED DESCRIPTION OF THE INVENTION

In a first embodiment, shown in environment of use in FIG. 4 and FIG. 8, the lumen of a catheter for implantation into the body is comprised of HOPG, described in further detail below. A HOPG transmission member 101 or 121 is in solid thermal conductive contact with the HOPG of the lumen, as well as with an external cooling element 102 or 122. When the external cooling element is operated, the cooling temperature is rapidly transmitted along the HOPG transmission element to the catheter.

Figure 1:
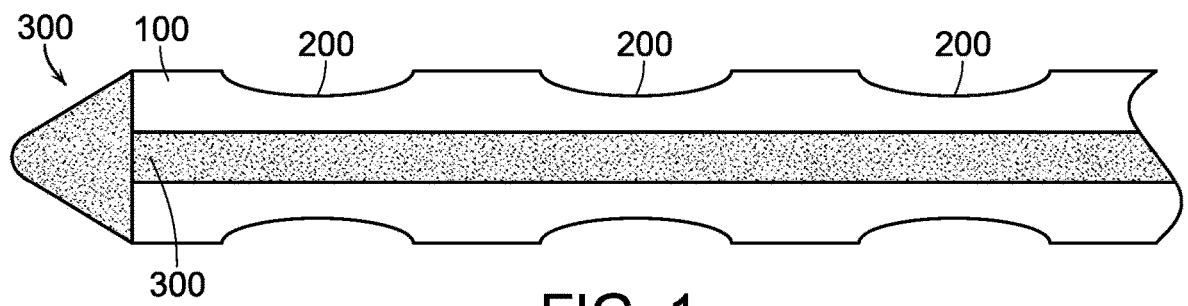
FIG. 1 is a side view of a first catheter lumen with HOPG sheets.
Figure 2:
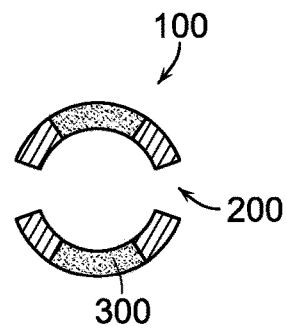
FIG. 2 is a front cross-sectional view of the first catheter lumen with HOPG sheets.

As shown in FIGS. 1, 2, 3 and 5, the catheter lumen comprises sections of HOPG 300. HOPG is biocompatible and bioinert, i.e. elicits little to no response from the body, and furthermore is known to have antithrombotic effects within the body, reducing the risk of clotting. Due to the flexibility of the HOPG, many configurations are possible. For instance, the HOPG 300 stretches axially along the length of the lumen, as shown in FIGS. 1 and 2. Or, as depicted in FIG. 4, the HOPG 300 is deposited in cross-sectional rings along the lumen. Alternatively, the HOPG 300 shown in FIG. 4 may be a thermally conductive frame attachable to a standard catheter, disposable or sterilizable and reusable.

Figure 3:
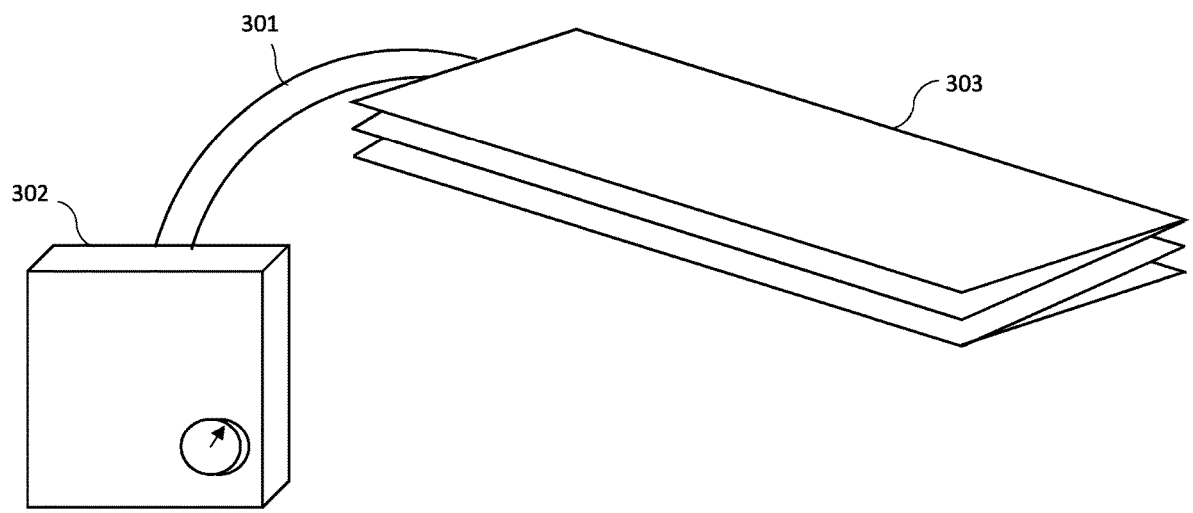
FIG. 3 is a perspective schematic of an implantable device with HOPG sheets.

A second embodiment, which is a generalized HOPG implant 303, is shown schematically in FIG. 3. Like the catheter lumens depicted in FIGS. 1, 2, and 4, the general HOPG implant can be implanted anywhere in the body. The general HOPG implant 303 can be a solid piece of HOPG, rather than a flexible and hollow lumen, and is shaped to maximize surface area. As shown in FIG. 3, the HOPG sheets of the implant have been folded in a fan or accordion-like structure. Other alternatives include: the HOPG may be rolled into a tube that is built into the catheter or multiple flexible "ribbons" of the graphite sheet may be affixed to the distal end of the catheter (like a horse's tail or cauda equina) which would float in the body cavity, cerebrospinal fluid or blood vessel. Although numerous designs are possible, the aforementioned designs would maximize exposed surface area and therefore the effects of heat conduction. Implant 303 is in solid thermal conductive connection with HOPG transmission member 301, which in turn is in thermal connection with external cooling element 302.

Figure 4:
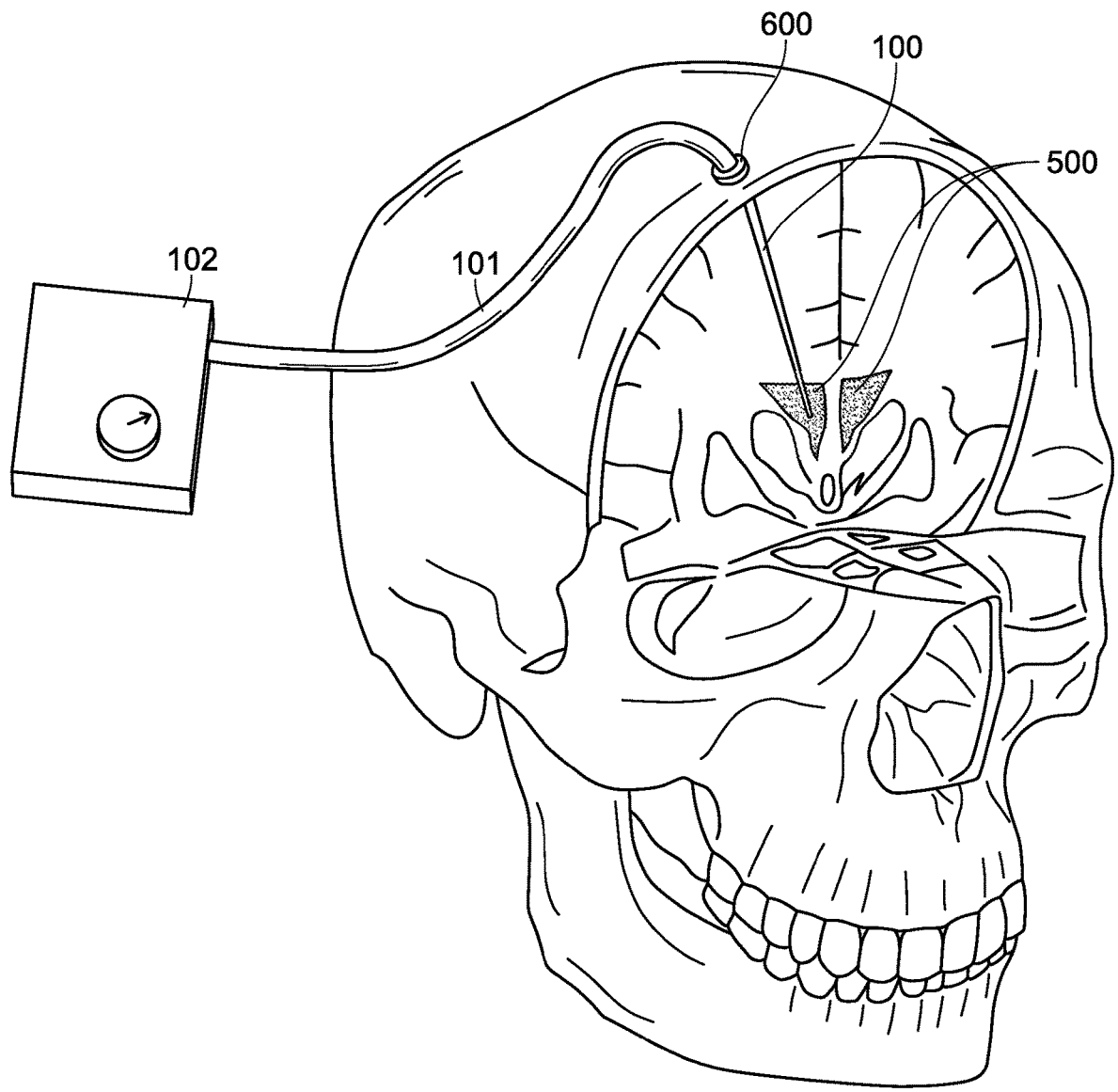
FIG. 4 is a perspective view of a hypothermia-induction catheter implantable into the brain ventricles.
Figure 5:
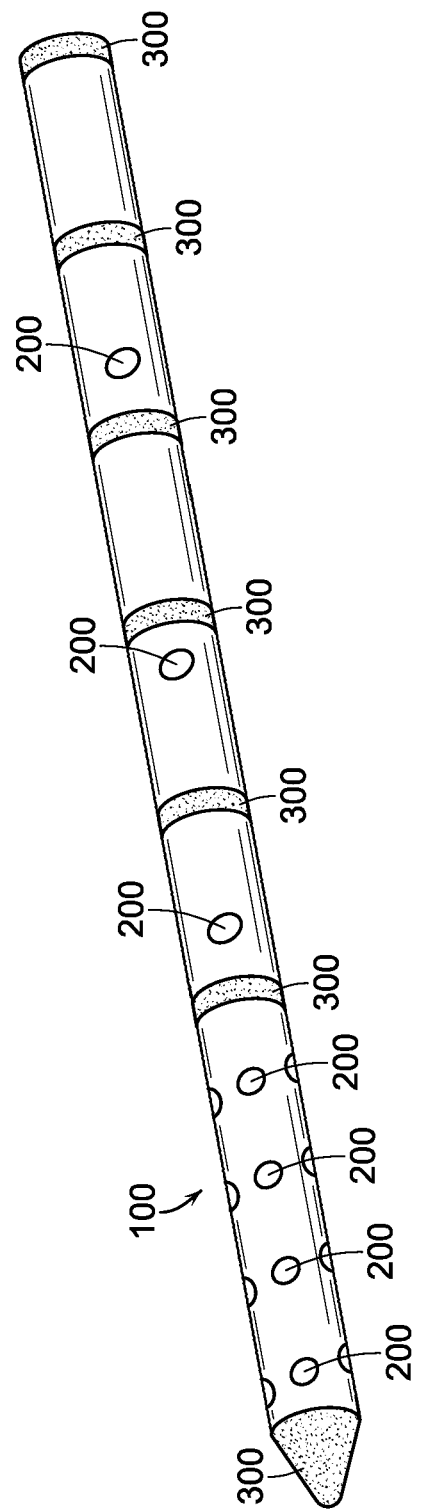
FIG. 5 is a perspective view of a second catheter lumen with HOPG sheets.
Figure 8:
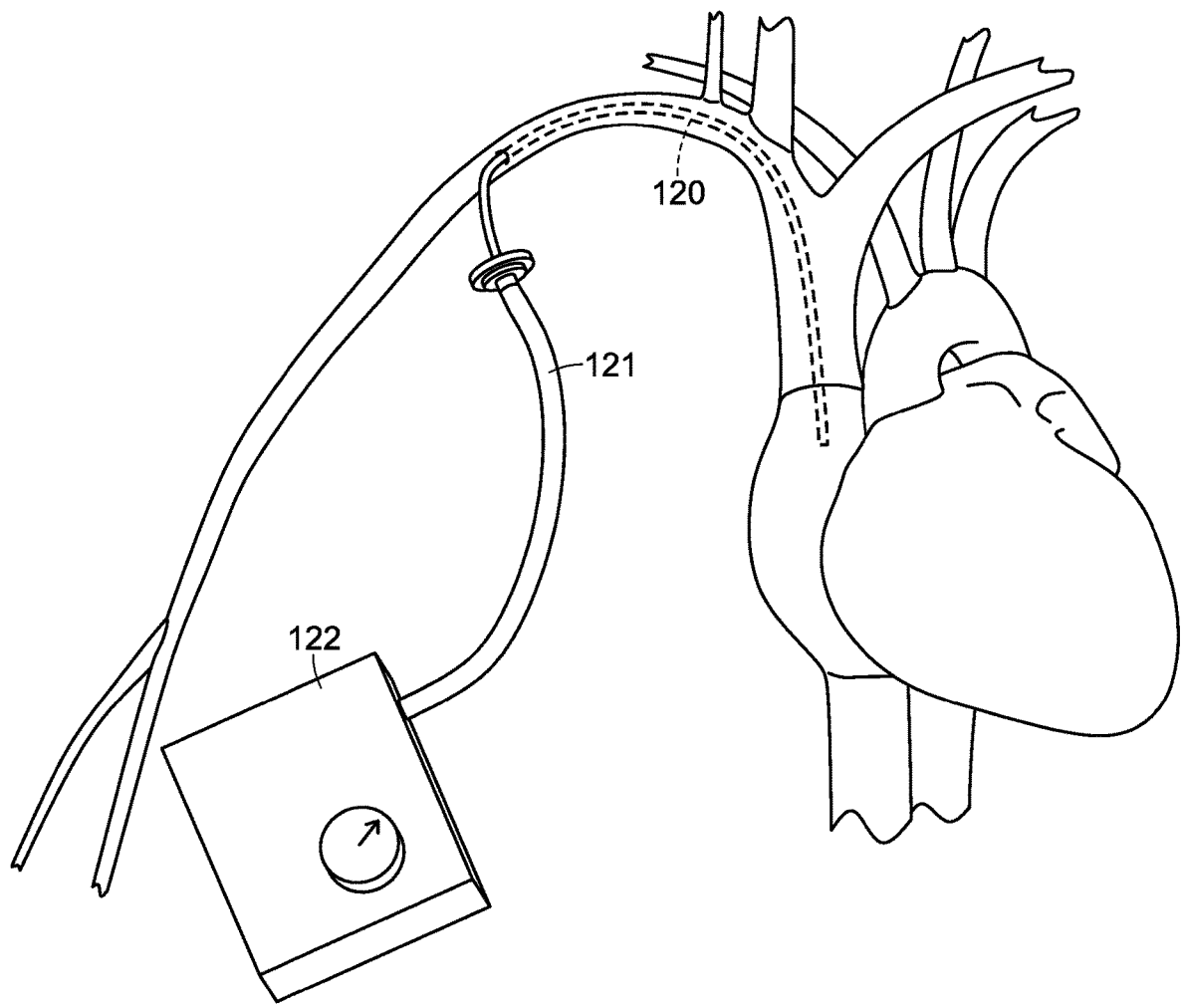
FIG. 8 is a schematic of a hypothermia-induction catheter implantable into the bloodstream in an environment of use.

Similarly, as shown in FIGS. 4 and 8. The HOPG of the catheters 100 or 120 is in solid thermal conductive connection with an HOPG transmission member 101 or 121 which is in turn in thermal conductive connection with an external cooling element 102 or 122. It should here be noted that the views depicted are schematics and do not limit the length or size of the HOPG transmission members. In other words, HOPG transmission members 101, 121, 301, 131, and 142 may be any length. Because of the high thermal conductivity of the HOPG, heat is rapidly conducted from the external cooling elements to the implants. Furthermore, due to the flexibility of HOPG and the freedom to design almost any shape, the HOPG transmission member and the HOPG of the catheters may be one and same. The external cooling element may be any cooling device, as simple as chilled liquid or gas such as frozen CO2, or more complex electronic devices such as heat pipes, Peltier machines, or other heat exchangers known in the art.

Preferably, the cooling catheter is implanted where circulation maximizes the induction of hypothermia. In the preferred embodiment, the cooling catheter is implanted into cerebrospinal fluid (CSF) during standard of care ventricle drainage procedures. The drainage catheter 100 is typically inserted into lateral ventrical 500 of the brain, as depicted in FIG. 4, and may comprise any combination of known monitoring sensors, such as pressure transducer, oxygen monitor, and temperature gauge. Openings 200 allow pressure to be alleviated as CSF enters catheter 100 through the openings and out of the skull. Due to the circulation of CSF throughout the brain and spinal cord, effective cooling may take place throughout the body, and especially in the brain and spinal cord where it is most needed. As such, the CSF cooling catheter both regulates intracranial pressure and induces hypothermia to further prevent ischemic injury. The cooling catheter may also be implanted into the bloodstream, as shown in FIG. 8. Not only is graphite biocompatible, but anti-thrombotic effects of HOPG further prevent clotting and strokes. Like the lumens shown in FIGS. 1, 2, 3 and 5, vascular cooling catheters may comprise openings for infusions of drugs and other fluids. The cooling catheter or cooling implant may also be inserted into the nasal or oral cavity, or natural orifices (such as, but not limited to, the oronasopharynx, esophagus, trachea, or colon/rectum) or elsewhere throughout the body.

Figure 6:
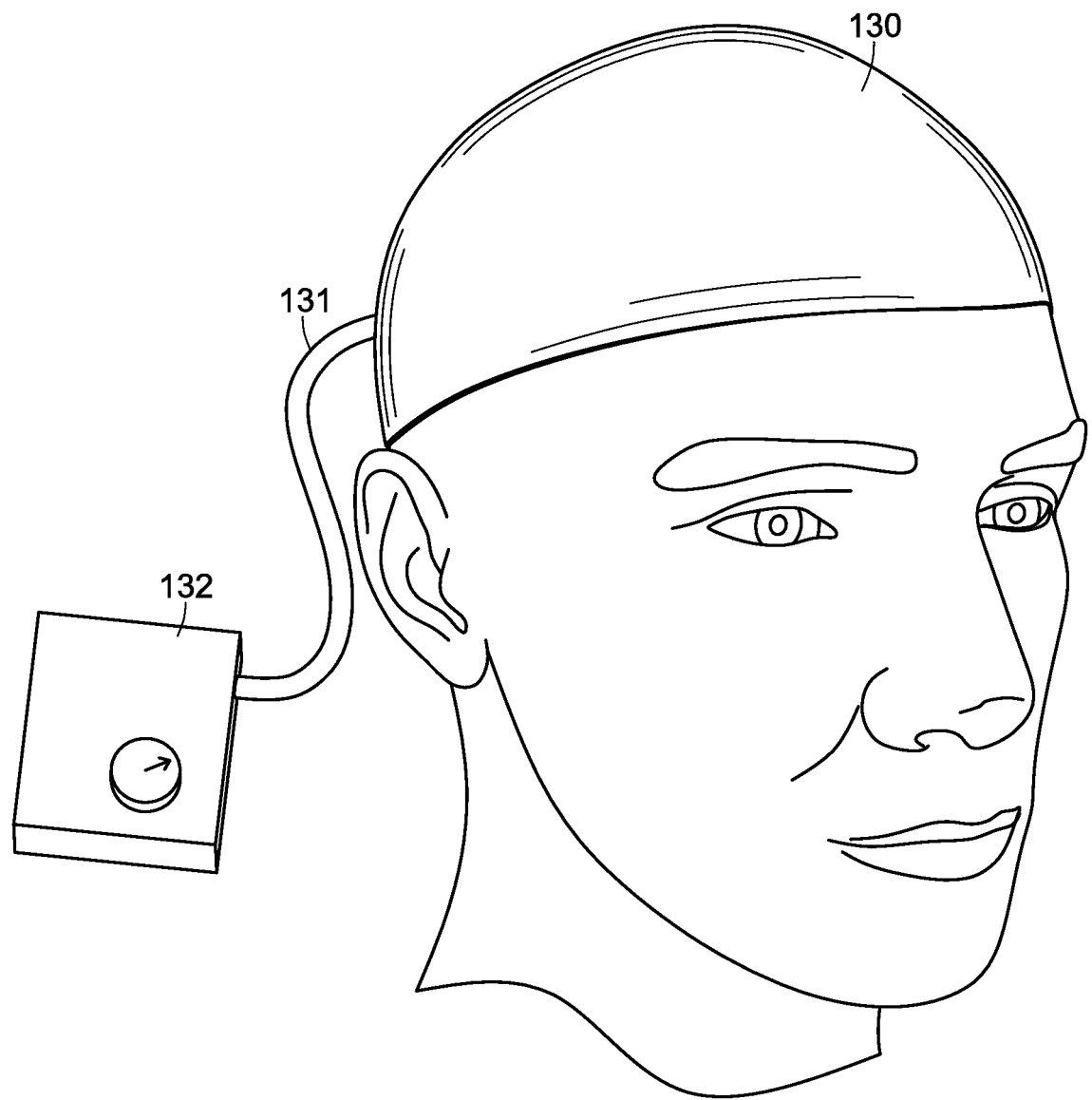
FIG. 6 is a perspective view of a cooling garment worn on the head in an environment of use.
Figure 7:
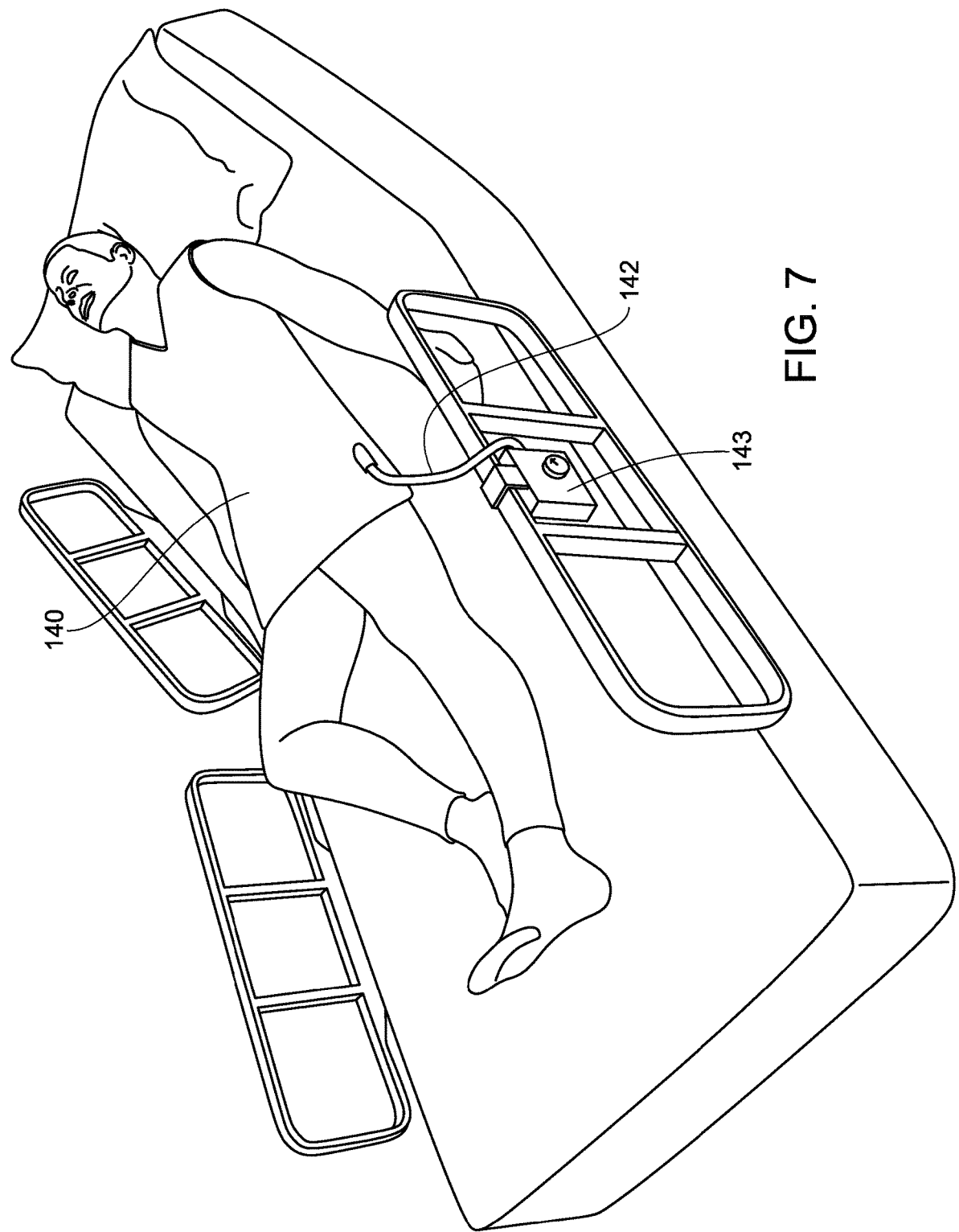
FIG. 7 is a perspective view of a cooling garment in an environment of use.

The concept of the present invention can also be applied to other cooling devices such as helmets, vests and blankets. For instance, as shown in FIG. 6, a cooling cap for placement over the head is comprised of HOPG 130, which is in solid thermal conductive connection with HOPG transmission member 131. Using an external cooling element 132, cooling temperatures are transferred via cooling member 131 to the graphite garment 130. In another embodiment, depicted in FIG. 7, a cooling garment or vest 140 is comprised of HOPG 140, which is in solid thermal conductive connection with HOPG transmission member 142. Using an external cooling element 143, cooling temperatures are transferred via transmission member 142 to the graphite garment 140. Due to the flexibility of the synthetic HOPG, the HOPG transmission member and the graphite of the catheters may be one and same. As in the case of the catheter devices, the external cooling element may be any cooling device, as simple as chilled liquid or gas such as frozen CO2, or electronic devices such as heat pipes, Peltier machines, or other heat exchangers known in the art.

Because the HOPG is biocompatible, it is suitable for contact with any section of the human body. Furthermore, the flexibility of the HOPG allows it to be incorporated into any type of garment or shape. The high thermal conductivity of the HOPG can also be utilized within braces, collars, immobilization devices, and casts to conduct away heat in order to maintain a more comfortable temperature for the patient. It is further contemplated that HOPG can be used in any garment for the purpose of cooling, and therefore has applications in clothing generally, such as leisure, athletics and other physical work. Optionally, electronic control may be connected to the cooling mechanism by wired or wireless connection.

The invention claimed is:
1. A device for inducing hypothermia comprised of:
   a. a Highly Oriented Pyrolytic Graphite (HOPG) implant comprised of one or more sheets of HOPG folded in an accordion-pattern;
   b. an HOPG transmission member in solid thermal conductive connection with the HOPG implant, such that the HOPG transmission member transfers heat to and from the HOPG implant by solid conduction; and
   c. an external cooling element for cooling the HOPG transmission member.
2. The device of claim 1, wherein the external cooling element comprises a cooled liquid or gas.
3. The device of claim 1, wherein the external cooling element comprises an electronic device.

* * * * *